United States Patent [19]

Gurtzgen

[11] Patent Number: 5,414,158
[45] Date of Patent: May 9, 1995

[54] METHOD OF PREPARING ALKOXY-MAGNESIUM HALIDES

[75] Inventor: Stefan Gurtzgen, Wuppertal, Germany

[73] Assignee: Witco GmbH, Bergkamen, Germany

[21] Appl. No.: 107,651

[22] Filed: Aug. 17, 1993

[30] Foreign Application Priority Data

Mar. 14, 1991 [DE] Germany .................. 41 08 204.4

[51] Int. Cl.6 ................. C07C 31/30; C07C 29/70
[52] U.S. Cl. .................. 568/851; 568/652; 568/715; 568/716; 568/812; 568/832; 568/834; 568/852
[58] Field of Search ............. 568/851, 832, 715, 812

[56] References Cited

U.S. PATENT DOCUMENTS

| | | | |
|---|---|---|---|
| 4,238,354 | 12/1980 | Dietz | 252/429 |
| 4,370,257 | 1/1983 | Imai et al. | 252/429 |
| 5,081,320 | 1/1992 | Wang et al. | 568/851 |
| 5,262,573 | 11/1992 | Wang et al. | 568/851 |

FOREIGN PATENT DOCUMENTS

| | | | |
|---|---|---|---|
| 0242801 | 10/1987 | European Pat. Off. | |
| 4108204 | 9/1992 | Germany | 568/851 |
| 16533 | 10/1992 | WIPO | 568/851 |

*Primary Examiner*—Werran B. Lone
*Attorney, Agent, or Firm*—Scully, Scott, Murphy & Presser

[57] ABSTRACT

It has surprisingly now been discovered that alkoxy-magnesium halides of the general formula ROMgX wherein R is an alkyl having from about 1 to 18 carbon atoms and X is a halide can be synthesized in an inert hydrocarbon in just one step process by reacting magnesium which has been preliminarily activated with small quantities (approximately 5 mol %) of magnesium alkyl with a substantially equimolar mixture of an alkyl halide and an alkanol. That is, the present invention provides a one step reaction process for preparing alkoxy-magnesium halides. This one step reaction process involves reacting magnesium metal which has been previously activated with a magnesium-alkyl compound, with an equimolar mixture of an alkyl halide and an alkanol. Yields in excess of 90% can be obtained by employing the inventive one step reaction process.

7 Claims, No Drawings

# METHOD OF PREPARING ALKOXY-MAGNESIUM HALIDES

FIELD OF THE INVENTION

The present invention relates to an improved method of preparing alkoxy-magnesium halides of the general formula ROMgX wherein R is an alkyl having from 1 to 18 carbon atoms and X is a halide in just one step by stoichiometrically converting magnesium that has been preliminarily activated with a magnesium-alkyl compound with an equimolar mixture of an alkyl halide and an alkanol, preferably a $\beta$-branched alkanol.

BACKGROUND OF THE INVENTION

Alkoxy-magnesium chlorides of general formula ROMgCl are employed for among other purposes preparing modified-support Ziegler-Natta catalysts, especially those based on titanium, for the polyolefin industry. They are superior to conventional Ziegler-Natta systems particularly because of their higher activity and higher stereospecificity in the polymerization of olefins.

The first potential educts that come to mind for preparing compounds of the ROMgX type are Grignard compounds of general formula RMgX in ether. This route, however, seems to be not generally accessible because of the problems involved in quantitatively removing the ether, which often disrupts polymerization. The literature describes many methods of preparing catalyst supports that include magnesium and a halide, especially chlorine. The first simple organometallic route to low melting-point products with or without hydrocarbon, however, is disclosed in European A 0 242 801, which describes preparing an alkyl-magnesium halide from magnesium and an alkyl halide in anhydrous hydrocarbons with oxygen compounds (alcohols, aldehydes, and ketones with 1 to 20 carbon atoms) in an inert-gas atmosphere at normal pressure and at a temperature of 40° to 200° C. Preferred are alcohols with 1 to 18 carbon atoms. Treatment with $\beta$-alkyl alkanols with 5 to 18 carbon atoms results in products that dissolve in hydrocarbons when 1.1 to 2.0 moles of alkanol are employed in terms of the magnesium. An essential characteristic of this process is that the reaction occurs in two steps. The Grignard compound is prepared in the first step and treated in the second step with the appropriate oxygen compound. When the alkyl halide and the alkanol were added simultaneously in just one step for comparison on the other hand (EPA 0 242 801, Examples A & B), the main products were magnesium dialkoxides.

SUMMARY OF THE INVENTION

It has surprisingly now been discovered that alkoxy-magnesium halides can also be synthesized in hydrocarbons in just one step if the magnesium is preliminarily activated with small amounts (approximately 5% molar) of magnesium alkyl.

DETAILED DESCRIPTION OF THE PRESENT INVENTION

The present invention accordingly addresses a method of preparing alkoxy-magnesium halides of general formula ROMgX characterized in that magnesium preliminarily activated with small amounts of a magnesium-alkyl compound is stoichiometrically reacted in just one step with an equimolar mixture of an alkyl halide ($R^1X$), especially an alkyl chloride, and an alkanol ($R^2OH$) in an inert hydrocarbon and an inert-gas atmosphere, whereby $R^1$ is a linear, branched, or cyclic hydrocarbon group with 1 to 8 carbon atoms and $R^2$ is a linear, branched, or cyclic hydrocarbon group with 1 to 20 carbon atoms.

Treatment with the 1:1 mixture of alkyl halide and alkanol, preferably an alkanol that branches at the $\beta$ position and has 5 to 18 carbon atoms, occurs in inert hydrocarbons at a temperature 50° to 150° C. and preferably 80° to 100° C. Adding another 0.1 to 1.0 moles of alkanol to improve the flow of the solutions, which are viscous when the alkanols are 2-substituted, and improve stability is practical (EPA 0 242 801). Yields are approximately 90% and the RO/Mg/X ratio is precisely or approximately 1:1:1.

Since the space-time yield of the process in accordance with the present invention is higher than that of the two-step process disclosed in EPA 0 242 801, the former is a more economical way to prepare alkoxy-magnesium halides, especially those that branch at position $\beta$. Furthermore, the direct, moderate, and continuous off-reaction of the "in situ" occurring Grignard compounds prevents too high a concentration of highly reactive organometallic compound, which obviously renders the process more reliable.

The following examples are given to illustrate the scope of the present invention. Because these examples are given for illustrative purposes only, the invention embodied therein should not be limited thereto.

EXAMPLES

Overall method of preparing ROMgX

Mixture I is heated to 100° C. in a flask of dry oxygen. Mixture II is added drop by drop for 45 minutes. The batch is preferably allowed to stand for 2 hours and Mixture III added (followed by 30 minutes of agitation at 100° C.) to reduce the viscosity and improve the stability of the solutions. The batch is then filtered.

The whole reaction takes approximately 3 hours.

| Example 1. Preparing 2-ethylhexoxymagnesium chloride | | |
|---|---|---|
| I: | 6.25 g | (0.257 moles) of powdered magnesium (BOMAG) |
| | 10.77 | (0.013 moles) of BOMAG-A (20% butyloctyl magnesium in heptane) |
| | 0.55 | of tributylaluminum |
| | 35.00 | of heptane |
| II: | 17.85 g | (0.193 moles) of butyl chloride |
| | 9.55 | (0.064 moles) of octyl chloride |
| | 35.20 | (0.270 moles) of 2-ethylhexanol |
| | 112.00 | of heptane |
| III: | 35.20 g | (0.270 moles) of 2-ethylhexanol |
| | 190.00 | of heptane |
| Yield from 420 g of filtrate: | | |
| Magnesium: | 1.46% (93% of theoretical) | |
| Chlorine: | 2.02 | |
| Alkal. Mg: | 0.73 | |

RO/Mg/Cl = 1:1:0.95

| Example 2. Preparing 2-hexyldecoxymagnesium chloride | | |
|---|---|---|
| I: | 6.25 g | (0.257 moles) of powdered magnesium |
| | 10.00 | (0.012 moles Mg) of BOMAG-A |
| | 0.51 | of tributylaluminum |
| II: | 17.85 g | (0.193 moles) of butyl chloride |
| | 9.55 | (0.064 moles) of octyl chloride |
| | 65.40 | (0.270 moles) of 2-hexyldecanol |
| | 112.00 | of heptane |
| III: | 65.40 g | (0.270 moles) of 2-hexyldecanol |
| | 176.00 | of heptane |
| Yield from 445 g of filtrate: | | |
| Magnesium: | 1.36% (92% of theoretical) | |
| Chlorine: | 2.03 | |

-continued

| Alkal. Mg: | 0.64 |

RO/Mg/Cl = 0.94:1:1

The above embodiments and examples are given to illustrate the scope and spirit of the present invention. These embodiments and examples will make apparent, to those skilled in the art, other embodiments and examples. These other embodiments and examples are within the contemplation of the present invention; therefore, the instant invention should be limited only by the appended claims.

I claim:

1. A method of preparing alkoxymagnesium halides of the general formula ROMgX wherein magnesium which has been preactivated by means of small amounts of an alkyl-magnesium compound is reacted stoichiometrically in a one-step process with an equimolar mixture of alkyl halide $R^1X$ and an alkanol $R^2OH$ in an inert hydrocarbon under an inert-gas atmosphere, where R is an alkyl from 1 to 18 carbon atoms, X is halide, $R^1$ is a linear, branched or cyclic hydrocarbon radical having 1–8 carbon atoms, and $R^2$ is a linear, branched or cyclic hydrocarbon radical having 1–20 carbon atoms.

2. The method according to claim 1 wherein the alkyl halide is alkyl chloride.

3. The method according to claim 1 wherein the magnesium employed is preactivated with 5mol % of alkyl-magnesium.

4. The method according to claim 3 wherein the alkanol employed is a β-branched alcohol having 5 to 18 carbon atoms.

5. The method according to claim 1 wherein the reaction is carried out at 50°–150° C.

6. The method according to claim 5 wherein the reaction is carried out at 80°–100° C.

7. The method according to claim 3 wherein the β-branched alcohol is employed in an excess of 0.1–1.0 moles at the end of the reaction in order to reduce the viscosity.

* * * * *